(12) United States Patent
Sparman

(10) Patent No.: US 9,138,448 B1
(45) Date of Patent: Sep. 22, 2015

(54) SUPPLEMENT COMPOSITION

(71) Applicant: Alfred Sparman, Bridgetown (BB)

(72) Inventor: Alfred Sparman, Bridgetown (BB)

( * ) Notice: Subject to any disclaimer, the term of this patent is extended or adjusted under 35 U.S.C. 154(b) by 3 days.

(21) Appl. No.: 14/294,849

(22) Filed: Jun. 3, 2014

(51) Int. Cl.
*A01N 65/00* (2009.01)
*A61K 36/185* (2006.01)
*A61K 36/11* (2006.01)
*A61K 31/375* (2006.01)
*A61K 36/00* (2006.01)

(52) U.S. Cl.
CPC ............. *A61K 36/185* (2013.01); *A61K 31/375* (2013.01); *A61K 36/00* (2013.01); *A61K 36/11* (2013.01)

(58) Field of Classification Search
CPC ....................................................... A61K 36/00
USPC ............................................................ 424/725
See application file for complete search history.

(56) References Cited

U.S. PATENT DOCUMENTS

2007/0264366 A1 * 11/2007 Chen et al. .................... 424/769

* cited by examiner

*Primary Examiner* — Michael Meller
(74) *Attorney, Agent, or Firm* — Alston & Bird LLP

(57) ABSTRACT

A supplement composition comprising materials derived from *M. Oleifera* and *B. Pinnatum* in combination with ascorbic acid. The composition has been observed to improve the health of patients to whom it was administered.

1 Claim, No Drawings

SUPPLEMENT COMPOSITION

FIELD OF THE INVENTION

This invention relates to a supplement composition comprising powders derived from plant leaves in combination with ascorbic acid. The composition has been observed to enhance proper cardiac functioning, inhibit inflammatory disorders and function as an antioxidant.

BACKGROUND OF THE INVENTION

Heart disease is the leading cause of death for both men and women in the United States. Reducing heart disease will improve the health of the population in general.

Heart disease has a number of facets including: coronary artery distress; abnormal heart rhythms; heart failure; heart valve disease; congenital heart disease; cardiomyopathy; and pericarditis. Coronary artery distress, or hardening of the arteries, deprives the heart of oxygen and nutrients. Abnormal heart rhythms are irregular, or abnormal, heart beat patterns, or arrhythmia. Heart failure occurs when the heart does not pump as it should. Heart valve disease occurs when a heart valve does not work correctly. Congenital heart disease is a defect in one or more structures of the heart or blood vessels that occur before birth. Cardiomyopathy is a disease of the heart muscle itself. Pericarditis is an inflammation of the lining that surrounds the heart.

Current medical advice to improve heart health includes: quitting smoking, lowering cholesterol levels, controlling high blood pressure, becoming more active, eating right, achieving and maintaining a healthy weight, managing stress and anger, and controlling diabetes.

All of these methods of prevention are arduous, time consuming and many times costly. Treating heart disease may include extensive medication, which also can be time consuming, expensive and have dangerous side effects. Ultimately, life threatening surgery may prove to be necessary.

Therefore, there is a continuing, demonstrated need to enhance cardiac function using compositions that are therapeutic but have few or preferrably virtually no side effects.

Inflammation-related disorders are characterized by a local or systemic, acute or chronic inflammation. Examples include inflammatory dermatoses, inflammatory bowel diseases, hypersensitivity lung diseases, asthma, and allergic rhinitis. Further, examples may include autoimmune diseases, acute and chronic inflammatory diseases, Sjogren's syndrome, human immunodeficiency virus infection, cancer, and tumor metastasis.

Modern anti-inflammatory agents are represented by two major groups: steroid and non-steroid pharmaceutical preparations. Despite the evident anti-inflammatory activity of either preparation, there are several limitations. For instance, a long-term application may cause unfavourable side effects, such as a damage of the gastrointestinal tract, i.e. nausea, vomiting, and stomach ulcer.

Moreover, these anti-inflammatory preparations can cause dysfunctions of the liver and kidney as well as bleedings, leukopenia to the extent of agranulocytosis, anemia. Further, side effects of a long-term administration of anti-inflammatory agents may include changes in the central nervous system, such as giddiness, headaches, excitation, insomnia, fatigability, edema. These factors limit the application of both steroid and non-steroid preparations in practical medicine. Thus, there is a current need for alternative low-toxic anti-inflammatory preparations.

While advances in early detection and adjuvant therapy for breast cancer have had a favorable impact on patient survival in general, patients who develop advanced metastatic breast cancer face a less favorable prognosis. Commonly used hormonal and chemotherapeutic agents can lead to transient regression of tumors and can also palliate symptoms related to cancer. However, these treatments are often accompanied by toxicities and intolerable side effects and eventually become ineffective in controlling advanced stage breast cancer and its symptoms. Improvements in survival are modest, even with newer targeted biological agents. Moreover, in most metastatic cancers resistance to available conventional treatment ultimately develops or excessive side effects are seen with conventional therapies.

Therefore, there is a need for therapies for treatment of patients having metastatic cancers. There is also a need for therapies with reduced, and more specifically minimal, toxicity for patients having metastatic cancers. In particular, there is a need for novel therapies with relatively low toxicity for the treatment of metastatic solid tumors, such as epithelial tumors, and more particularly breast and ovarian cancers.

Free radicals have come to be appreciated for their importance to human health and disease. Many common and life-threatening diseases, including atherosclerosis, cancer, and aging, may have free radical reactions as an underlying mechanism of injury. One of the most common types of radicals is the reactive oxygen species (ROS). These are the products of normal cell respiration and metabolism and are generally regulated by cellular defense systems present in the body. Such cellular defense systems reduce the amount of damage that free and reactive species radicals may cause by scavenging free radicals or enzymatically converting the free radicals to less toxic chemical species, thereby serving a physiological role as antioxidants.

Non-enzymatic antioxidants can react with free radicals directly and self-oxidized (therefore no longer available to quench free radicals); or one antioxidant may act as a reducing agent and another antioxidant oxidized in cyclical fashion (e.g., the interaction of ascorbic acid and alpha-tocopherol). Other non-enzymatic free radical scavengers have been used experimentally with varying results (e.g. mannitol, PBS, etc.); their clinical use is severely limited due to their toxicities. Other synthetic antioxidants, e.g., BHA (butylated hydroxy anisole), BHT (butylated hydroxy toluene) and NDGA (nordihydro guaiaretic acid) may cause allergic reactions. These agents may also cause oncogenesis due to their strong toxicity in the body, and be easily disrupted by heat due to temperature sensitivity. Therefore, there is a need for developing novel compositions therapeutically effective as anti-oxidants.

Diabetes mellitus is a worldwide health threat of increasing magnitude, and is considered a major health risk both in developed and in developing countries. Type II diabetes accounts for the vast majority of the cases involving diabetes and it is the seventh leading cause of death in the United States. It appears that the major contributing factor to the incidence of Type II diabetes is being overweight. In the United States alone, it is estimated that over 17.6 million individuals have been diagnosed as having diabetes. It is estimated that an additional 5.7 million individuals are unaware they have diabetes. Moreover, there are about 57 million Americans who are considered pre-diabetic.

Type II diabetes is also known as non-insulin dependent diabetes. It generally manifests itself as an inability to adequately regulate blood-glucose levels. This is as opposed to Type I diabetes which is characterized by defects in pancreatic production of insulin. In other words, it appears that Type II sufferers suffer from too little insulin or insulin resistance. The factors that have been identified in contributing to these Type II factors include one or more of obesity, genetic background, age, diet, and blood chemistry. Type II is frequently called adult onset because diet is a factor, but it can arise at virtually any age.

The results of diabetes Type II cause glucose levels to rise in the blood and urine. These increases, in turn, can cause hunger, urination, thirst and metabolism related issues. If the condition is not treated, the most common serious results include: heart disease, kidney disease, and blindness. Several treatments are currently being used. Because obesity is frequently a causal agent in diabetes, diet and exercise are usually a front line defense. Therapeutic agents are also used as a second line of defense, including use of insulin or pharmaceuticals that reduce blood and urine levels of glucose.

Several drugs are in current use for diabetes Type II, including insulin segretagogues, glucose lowering effectors, GLP-1 analogs, DPPIV, activators of the peroxisome proliferator activated receptor-gamma and alpha-glucosidase inhibitors. Because these current treatments have side effects, there remains a need for alternative therapies to treat type II diabetes.

A combination of risk factors or clinical conditions that occur together more often than by a mere chance that results in cardiovascular disease and type II diabetes mellitus have become known as the "metabolic syndrome." These clinical conditions include, but are not limited to, raised blood pressure, dyslipidemia (raised triglycerides and lowered high-density lipoprotein cholesterol), raised fasting glucose, and central obesity.

Metabolic syndrome is frequently associated with, or strongly suggests, prognosis or predicts development of a constellation of co-morbidity including diabetes, hypertension, coronary artery disease, vascular disease, chronic heart failure and chronic kidney disease. Metabolic syndrome is also frequently described as the underlying cause of serious cardiorenal diseases such as hypertension, coronary artery disease, vascular disease, chronic heart failure and chronic kidney disease. In addition, metabolic syndrome can also cause organ fibrosis (e.g., heart, lung and kidney).

Therefore, there is a need for a therapeutic treatment of metabolic syndrome or clinical conditions associated with metabolic syndrome to ameliorate or prevent these diseases

SUMMARY OF THE INVENTION

The primary objective of the present invention is to provide a new and improved supplement composition, including components from the leaves of *M. Oleifera* and *B. Pinnatum* plants in combination with ascorbic acid.

It is one aspect of the present invention to provide a new and improved supplement composition for improving the health of a person.

It is another aspect of the present invention to provide a new and improved supplement composition for treating heart diseases.

DETAILED DESCRIPTION OF THE INVENTION

The primary objective of the present invention is to provide a new and improved supplement composition, including components from the leaves of *M. Oleifera* and *B. Pinnatum* plants in combination with ascorbic acid.

A preferred method of producing a composition according to the present invention is as follows.

*M. Oleifera*—Fresh leaves harvested from *M. Oleifera* trees are washed with water for three times. The washed leaves are spread out in a tray and then air-dried at room temperature for ten (10) days. Alternatively, the washed leaves may be freeze dried. The dried leaves are further pulverized by a milling machine. The leaf powder is tested to ensure the absence of bacteria, pesticide and other impurities using conventional analytical tests, such as the McFarland Standard.

*B. Pinnatum*—Fresh leaves harvested from *B. Pinnatum* trees are washed with water for three times. The washed leaves are spread out in a tray and then air-dried at room temperature for ten (10) days. Alternatively, the washed leaves may be freeze dried. The dried leaves are further pulverized by a milling machine. The leaf powder is tested to ensure the absence of bacteria, pesticide and other impurities using conventional analytical tests, such as the McFarland Standard.

The leaf powders from the processes outlined above are then mixed with a supplemental amount of ascorbic acid. The resultant mixture is finally manufactured in a capsule form, a tablet, or a liquid extract.

In general, the composition of the present invention comprises between about 1 and 1300 parts by weight of material from the leaves of the *M. Oleifera* plant; between about 1 and 200 parts by weight of material from the leaves of the *B. Pinnatum* plant; and between about 1 and 2000 parts by weight of ascorbic acid. More preferably, the supplement comprises *M. Oleifera* leaf powder between about 1 and 750 parts by weight (mg); *B. Pinnatum* leaf powder between about 1 and 100 parts by weight (mg); and ascorbic acid between about 1 and 1000 parts by weight (mg).

It is desired that the ratio of *M. Oleifera* leaf powder to *B. Pinnatum* leaf powder to said ascorbic acid is between about 10:1:10 and 50:10:4. Other desired ratios of *M. Oleifera* leaf powder to *B. Pinnatum* leaf powder to said ascorbic acid include about 75:20:100 and 75:5:4. It is further preferred that the ratio of these materials is between about 7.5:1:10 and 7.5:1:0.4.

The following examples are illustrative of some of the products and methods of making the same falling within the scope of the present invention. They are, of course, not to be considered in any way restrictive of the scope of the invention. Numerous changes and modifications can be made with respect to the invention.

A preliminary study was undertaken with a group of 40 patients who had a) high levels of cholesterol; b) elevated blood pressure; or c) both.

Ten of these patients were given a sugar capsule placebo once a day for 3 months. The other thirty patients were given a capsule comprising 750 mg of *M. Oleifera* leaf powder and 100 mg of *B. Pinnatum* leaf powder admixed with 1000 mg of ascorbic acid daily for 3 months. Beginning one (1) day after the first dose, the patients had a weekly follow-up visit. The weekly follow-up visits continued for 3 months.

Among the 40 patients participating in the preliminary study, 87.5% of them have hyperlipidemia; 75% of them have hypertension; 30% of them have corinary artery disease; 17.5% of them have erectile dysfunction; 82.5% of them have arthritis; 8% of them have cardiomyopathy; and 62.5% of them have diabetes.

After the treatment with the instant supplement composition for three months, each group of the aforementioned experimental patients have achieved 30-100% improvement. Specifically, after taking the claimed supplement composition for three months, 20% of the patients with hyperlipidemia had lower cholesterol levels and stopped taking conventional medicine; 14.7% of the patients with hypertension now had blood pressure in the normal range and stopped conventional medicine; 50% of the patients with erectile dysfunction no longer had the symptoms and stopped conventional medicine; 30% of the patients with arthritis were no longer suffering from the symptoms and stopped conventional medicine; and 15% of the patients with diabetes had normal sugar levels and stopped conventional medicine.

In other examples, a capsule containing 750 mg of *M. Oleifera* leaf powder and 100 mg of *B. Pinnatum* leaf powder admixed with 40 mg of ascorbic acid is given to kids with Type 1 diabetes, congenital dislipidemia, early onset hypertension and early cardiomyopathy. It is anticipated that the symptoms associated with Type 1 diabetes, congenital dislipidemia, early onset hypertension and early cardiomyopathy will decrease after three months of taking one capsule a day.

A capsule containing 750 mg of *M. Oleifera* leaf powder and 100 mg of *B. Pinnatum* leaf powder admixed with 90 mg of ascorbic acid is given to adults with hyperlipidemia, hypertension, corinary artery disease, erectile dysfunction, arthritis, cardiomyopathy, and diabetes. It is anticipated that the symptoms associated with hyperlipidemia, hypertension, corinary artery disease, erectile dysfunction, arthritis, cardiomyopathy and diabetes will decrease after three months of taking one capsule a day.

A capsule containing 750 mg of *M. Oleifera* leaf powder and 100 mg of *B. Pinnatum* leaf powder admixed with 120 mg of ascorbic acid is given to adults with hyperlipidemia, hypertension, corinary artery disease, erectile dysfunction, arthritis, cardiomyopathy and diabetes. It is anticipated that the symptoms associated with hyperlipidemia, hypertension, corinary artery disease, erectile dysfunction, arthritis, cardiomyopathy and diabetes will decrease after three months of taking one capsule a day.

Pills can be formed by using an excipient, such as glucose, lactose, starch, cacao butter, hydrogenated vegetable oil, kaolin and talc; a binder, such as powdered gum Arabic, powdered tragacanth, gelatin and ethanol; a disintegrating agent, such as laminaran and agar; and other carriers.

Capsules can be typically prepared by mixing the ingredients of the present invention with the various conventional carriers and other ingredients described above, and encapsulating the mixture in a hard gelatin capsule, a soft gelatin capsule or other capsules using known techniques.

Liquid extracts may be formed by using clean leaves from *M. Oleifera* or *B. Pinnatum* that have been finely chopped. After being chopped, the leaves are placed to soak in vegan certified glycerine for a minimum of eight (8) days to one (1) month. The mixture is then filtered by using a fine seive/cheesecloth to remove any traces of the leaves. The collected solution after filtration is further mixed with puried water. The extracts are then stored at room temperature.

Liquid extracts from *M. Oleifera* and *B. Pinnatum* are blended to create a liquid having the extractant from 750 mg *M. Oleifera* and 100 mg *B. Pinnatum* per teaspoon of the blended liquid. To the blended liquid is added 1000 mg ascorbic acid. A teaspoon of the resulting liquid is given daily to a person in need.

What is claimed is:

1. A capsule consisting essentially of 1-750 parts of *Bryophyllum pinnatum* leaf powder, 1-100 parts of *Moringa oleifera* leaf powder and 1-1000 parts of ascorbic acid.

* * * * *